(12) United States Patent
Sirinyan et al.

(10) Patent No.: US 6,300,348 B1
(45) Date of Patent: *Oct. 9, 2001

(54) PESTICIDE FOR PARASITIC INSECTS AND ACARIDS ON HUMANS

(75) Inventors: Kirkor Sirinyan, Bergisch Gladbach; Ulrich Heukamp, Kürten; Hubert Dorn, Wuppertal; Ronald Helmut Stöcker, Monheim; Rainer Sonneck, Leverkusen, all of (DE); Rosemary Peter, River Club (ZA)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/142,892
(22) PCT Filed: Mar. 21, 1997
(86) PCT No.: PCT/EP97/01427
  § 371 Date: Sep. 16, 1998
  § 102(e) Date: Sep. 16, 1998
(87) PCT Pub. No.: WO97/37544
  PCT Pub. Date: Oct. 16, 1997

(30) Foreign Application Priority Data

Apr. 3, 1996 (DE) .............................. 196 13 334

(51) Int. Cl.$^7$ .......................... H01N 51/00; H01N 43/28; H01N 25/02
(52) U.S. Cl. .......................... 514/336; 514/336; 514/341; 514/830
(58) Field of Search .................................. 514/336, 341, 514/830

(56) References Cited

U.S. PATENT DOCUMENTS 5,059,593 * 10/1991 Stendel et al. ..................... 514/65
5,504,081 * 4/1996 Lohr et al. ....................... 514/225

OTHER PUBLICATIONS

Dorn et al. (CA 124:79467 abstract of EP 682869), 1995.*
Ogawa et al. (CA 118:75401 abstract of JP 04279503), 1992.*

* cited by examiner

Primary Examiner—Sabiha Qazi
(74) Attorney, Agent, or Firm—Joseph C. Gil; Godfried R. Akorli

(57) ABSTRACT

The present invention relates to formulations for the dermal control of parasitic insects on humans, having the following composition agonists or antagonists of the nicotinergic acetylcholine receptors of insects in a concentration of from 0.0001 to 12.5% by weight based on the overall weight of the formulation;

solvents from the group of the cyclic carbonates in a concentration of from 2.5 to 99.9999% by weight based on the overall weight of the formulation;

if desired, further solvents from the group consisting of the alcohols in a concentration of from 0 to 95% by weight based on the overall weight of the formulation;

if desired, further auxiliaries from the group of the thickeners, spreading agents, colorants, antioxidants, propellants, preservatives, adhesives, emulsifiers, in a concentration of from 0 up to 30% by weight based on the overall weight of the formulation.

4 Claims, No Drawings

PESTICIDE FOR PARASITIC INSECTS AND ACARIDS ON HUMANS

The present invention relates to formulations for the dermal control of parasitic insects and mites on humans by means of agonists or antagonists of the nicotinergic acetylcholine receptors of insects.

Agonists or antagonists of the nicotinergic acetylcholine receptors of insects are known. They include the nicotinyl insecticides and, very particularly, the chloronicotinyl insecticides.

PCT application WO 93/24 002 discloses that certain 1-[N-(halo-3-pyridylmethyl)]-N-methylamino-1-alkylarnino-2-nitroethylene derivatives are suitable for systemic use against fleas in domestic animals. According to WO 93/24 002, the nonsystemic—i.e. dermal—mode of application is unsuitable for the control of fleas on domestic animals.

This invention, then, provides novel formulations for the dermal application of agonists or antagonists of the nicotinergic acetylcholine receptors of insects which are particularly suitable for dermal control of parasitic insects and mites on humans.

The formulations according to the invention have the following composition:

agonists or antagonists of the nicotinergic acetylcholine receptors of insects in a concentration of from 0.0001 to 20% by weight based on the overall weight of the formulation;

solvents from the group of the cyclic carbonates in a concentration of from 2.5 up to 99.9999% by weight based on the overall weight of the formulation;

if desired, further solvents from the group of the alcohols in a concentration of from 0 to 95% by weight based on the overall weight of the formulation;

if desired, further auxiliaries from the group of the thickeners, spreading agents, colorants, antioxidants, propellants, preservatives, adhesives, emulsifiers, in a concentration of from 0 up to 30% by weight based on the overall weight of the formulation.

Agonists or antagonists of the nicotinergic acetylcholine receptors of insects are known, for example, from European Offenlegungsschriften (European Published Applications) Nos. 580 553, 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389; German Offenlegungsschriften (German Published Specifications) Nos. 3 639 877, 3 712 307; Japanese Offenlegungsschriften (Japanese Published Applications) Nos. 03 220 176, 02 207 083, 63 307 857, 63 287 764, 03 246 283, 04 9371, 03 279 359, 03 255 072, U.S. Pat. Nos. 5,034,524, 4,948,798, 4,918,086, 5,039,686, 5,034,404; PCT Applications Nos. WO 91/17 659, 91/4965; French Application No. 2 611 114; Brazilian Application No. 88 03 621.

The compounds described in these publications and their preparation are hereby expressly incorporated herein by reference.

These compounds can be advantageously represented by the general formula (I)

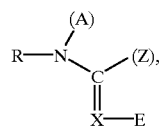

(I)

in which

R represents, hydrogen, optionally substituted radicals from acyl, alkyl, aryl, aralkyl, heteroaryl or heteroarylalkyl;

A represents a monofunctional group from hydrogen, acyl, alkyl, aryl, or represents a bifunctional group which is linked to the radical Z;

E represents an electron-withdrawing radical;

X represents the radicals —CH= or =N—, it being possible for the radical —CH= instead of an H atom to be linked to the radical Z;

Z represents a monofunctional group from alkyl, —O—R, —S—R,

or represents a bifunctional group which is linked to the radical A or to the radical X.

Particularly preferred compounds of the formula (I) are those in which the radicals have the following meaning:

R represents hydrogen and represents optionally substituted radicals from acyl, alkyl, aryl, aralkyl, heteroaryl, heteroarylalkyl.

Acyl radicals which may be mentioned are formyl, alkylcarbonyl, arylcarbonyl, alkylsulfonyl, arylsulfonyl, (alkyl)-(aryl)-phosphoryl, which may in turn be substituted.

As alkyl there may be mentioned $C_{1-10}$-alkyl, especially $C_{1-4}$-alkyl, specifically methyl, ethyl, i-propyl, sec- or t-butyl, which may in turn be substituted.

As aryl there may be mentioned phenyl, naphthyl, especially phenyl.

As aralkyl there may be mentioned phenylmethyl, phenethyl.

As heteroaryl there may be mentioned heteroaryl having, up to 10 ring atoms and N, O, S, especially N, as hetero atoms. Specifically there may be mentioned thienyl, furyl, thiazolyl, imidazolyl, pyridyl, benzothiazolyl, As heteroarylalkyl there may be mentioned heteroarylmethyl, heteroarylethyl having up to 6 ring atoms and N, O, S, especially N, as hetero atoms.

Substituents which may be listed by way of example and preference are: alkyl having preferably 1 to 4, in particular 1 or 2 carbon atoms, such as methyl, ethyl, n- and i-propyl and n-, i- and t-butyl; alkoxy having preferably 1 to 4, in particular 1 or 2 carbon atoms, such as methoxy, ethoxy, n- and i-propyloxy and n-, i- and t-butyloxy; alkylthio having preferably 1 to 4, in particular 1 or 2 carbon atoms, such as methylthio, ethylthio, n- and i-propylthio and n-, i- and t-butylthio; halogenoalkyl having preferably 1 to 4, in particular 1 or 2 carbon atoms and preferably 1 to 5, in particular 1 to 3 halogen atoms, the halogen atoms being identical or different and being preferably fluorine, chlorine or bromine, especially fluorine, such as trifluoromethyl; hydroxyl; halogen, preferably fluorine, chlorine, bromine and iodine, especially fluorine, chlorine and bromine; cyano; nitro; amino; monoalkyl- and dialkylamino having preferably 1 to 4, in particular 1 or 2 carbon atoms per alkyl group, such as methylamino, methyl-ethylamino, n- and i-propylamino and methyl-n-butylamino; carboxyl; carbalkoxy having preferably 2 to 4, in particular 2 or 3 carbon atoms, such as carbomethoxy and carboethoxy; sulpho (—SO$_3$H); alkylsulfonyl having preferably 1 to 4, in particular 1 or 2 carbon atoms, such as methylsulfonyl and ethylsulfonyl; arylsulfonyl having preferably 6 or 10 aryl carbon atoms, such as phenylsulfonyl, and also heteroarylamino and heteroarylalkylamino such as chloropyridylamino and chloropyridylmethylamino.

A particularly preferably represents hydrogen and represents optionally substituted radicals from acyl, alkyl, aryl, which preferably have the meanings given for R. A additionally represents a bifunctional group. There may be mentioned optionally substituted alkylene having 1–4, in particular 1–2 C atoms, substituents which may be mentioned being the substituents listed earlier above, and it being possible for the alkylene groups to be interrupted by hetero atoms from the group consisting of N, O, S.

A and Z may, together with the atoms to which they are attached, form a saturated or unsaturated heterocyclic ring. The heterocyclic ring can contain a further 1 or 2 identical or different hetero atoms and/or hetero groups. Hetero atoms are preferably oxygen, sulfur or nitrogen, and hetero groups are preferably N-alkyl, where the alkyl in the N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are imidazolidine, pyrrolidine, piperidine, piperazine, hexamethyleneimine, hexahydro-1,3,5-triazine, hexahydrooxodiazine, morpholine, each of which may optionally be substituted, preferably by methyl.

E represents an electron-withdrawing radical, in which context particular mention may be made of NO$_2$, CN, halogenoalkylcarbonyl such as 1,5-halogeno-C$_{1-4}$-carbonyl, especially COCF$_3$.

X represents —CH= or —N=

Z represents optionally substituted radicals alkyl, —OR, —SR, —NRR, where R and the substituents preferably have the meaning given above.

Z can form, apart from the abovementioned ring, and together with the atom to which it is attached and with the radical

instead of X, a saturated or unsaturated heterocyclic ring. The heterocyclic ring can contain a further 1 or 2 identical or different hetero atoms and/or groups. The hetero atoms are preferably oxygen, sulfur or nitrogen, and the hetero groups are preferably N-alkyl, in which case the alkyl or N-alkyl group preferably contains 1 to 4, in particular 1 or 2 carbon atoms. As alkyl there may be mentioned methyl, ethyl, n- and i-propyl and n-, i- and t-butyl. The heterocyclic ring contains 5 to 7, preferably 5 or 6 ring members.

Examples of the heterocyclic ring which may be mentioned are pyrrolidine, piperidine, piperazine, hexamethyleneimine, morpholine and N-methylpiperazine.

As compounds which may be used with very particular preference in accordance with the invention, mention may be made of compounds of the general formulae (II) and (III):

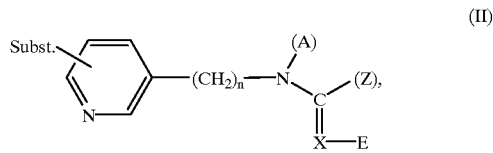

(II)

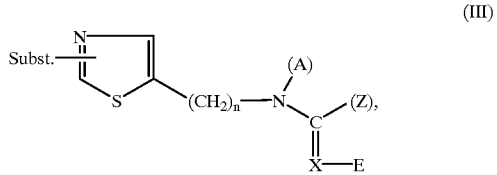

(III)

in which n represents 1 or 2, subst. represents one of the above-listed substituents, especially halogen, very particularly chlorine, A, Z, X and E have the meanings given above, Specifically, the following compounds may be mentioned:

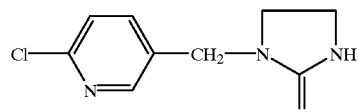

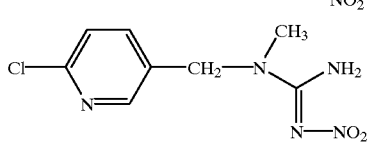

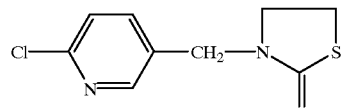

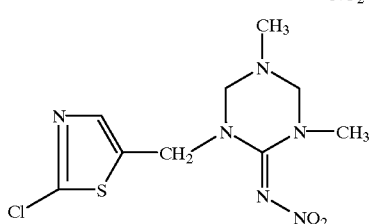

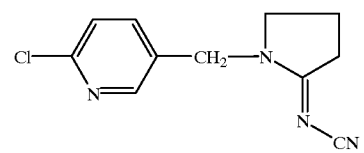

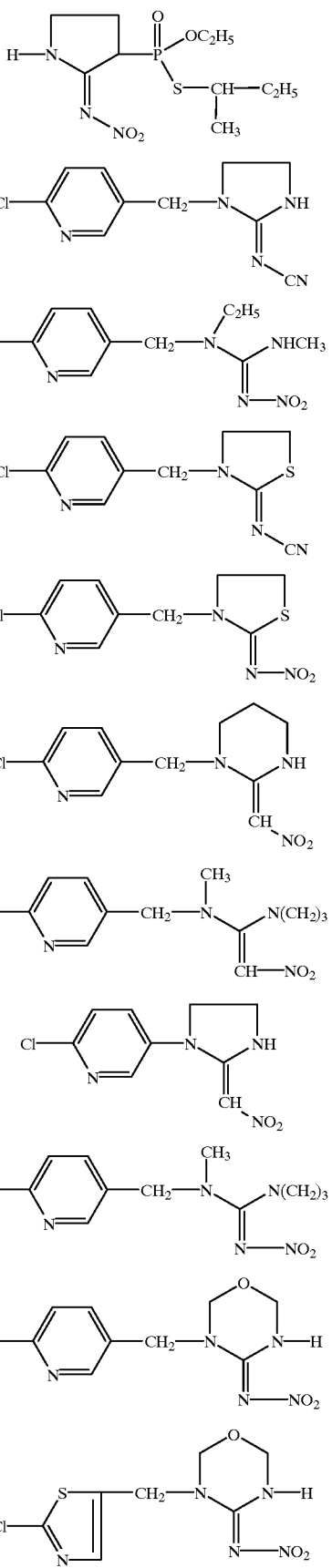
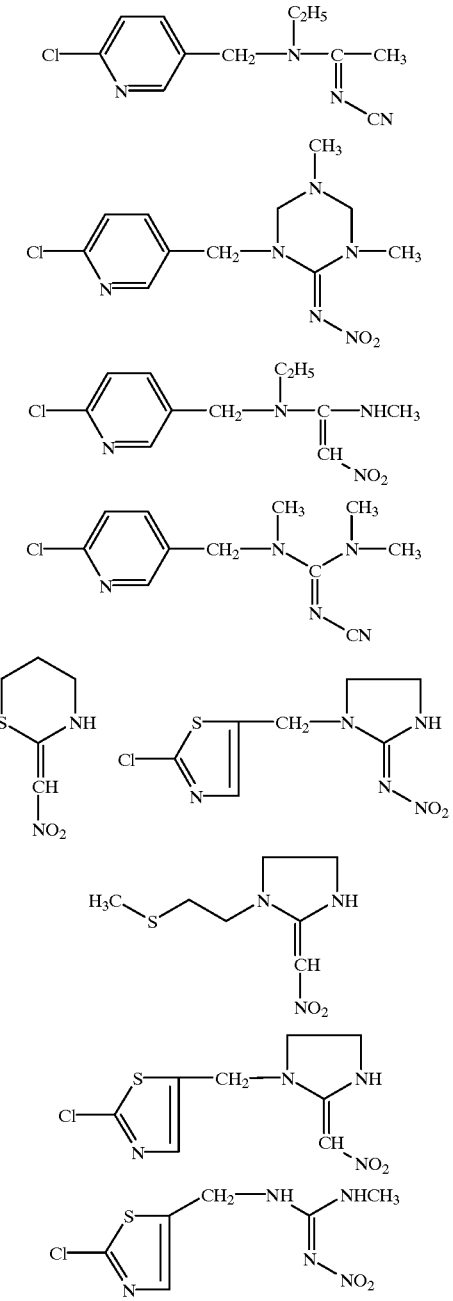

The formulations according to the invention contain the active substance in concentrations of from 0.0001 to 20% by weight, preferably from 0.1 to 12.5% by weight, particularly preferably from 1 to 10%.

Preparations which are diluted before use contain the active substance in concentrations of from 0.5 to 90% by weight, preferably from 1 to 50% by weight.

Suitable solvents are: water, cyclic carbonates. Preferred cyclic carbonates are ethylene carbonate, propylene carbonate. Particular preference is given to propylene carbonate.

They are present in a concentration of from 2.5 to 99.9999% by weight, preferably from 7.5 to 90% by weight, particularly preferably from 10 to 90% by weight.

Suitable additional solvents are: cyclic and acyclic alcohols, such as isopropanol, ethanol, diethylene glycol, 2-octyl-1-dodecanol and tetrahydrofurfuryl alcohol.

They are present in a concentration of at least 0 to 95% by weight, preferably from 5 to 30% by weight, particularly preferably from 5 to 20% by weight.

Suitable further auxiliaries are: preservatives such as benzyl alcohol (not required if already present as solvent), trichlorobutanol, p-hydroxybenzoic esters, n-butanol and water as solubility enhancer.

They are present in a concentration of from 0 to 15% by weight, preferably from 2.5 to 12.5% by weight, particularly from 2.5 to 10.0% by weight.

The sum of active compounds, solvents and auxiliaries has to be 100% by weight.

Thickeners are, for example, inorganic thickeners such as bentonites, colloidal silicic acid, aluminum monostearate, organic thickeners such as cellulose derivatives, polyvinyl alcohols, polyvinylpyrrolidones and copolymers thereof, acrylates and methacrylates.

Colorants which may be mentioned are all colorants approved for use in drugs which may be dissolved or suspended.

Auxiliaries are also spreading oils such as di-2-ethylhexyl adipate, isopropyl myristate, dipropylene glycol pelargonate, cyclic and acyclic silicone oils such as dimeticones and also co- and terpolymers thereof with ethylene oxide, propylene oxide and formalin, fatty acid esters, triglycerides, fatty alcohols.

Antioxidants are, for example, sulfites or metabisulfites such as potassium metabisulfite, ascorbic acid, butylated hydroxytoluene, butylated hydroxyanisole, tocopherol.

Light stabilizers are, for example, substances from the class of the benzophenones or Novantisol acid.

Adhesives are, for example, polymeric thickeners, for example, cellulose derivatives, starch derivatives, polyacrylates, naturally occurring polymers such as alginates, gelatin.

Auxiliaries are also emulsifiers such as nonionic surfactants, for example polyoxyethylated castor oil, polyoxyethylated sorbitan monooleate, sorbitan monostearate, glycerol monostearate, polyoxyethyl stearate, alkylphenol polyglycol ethers;

ampholytic surfactants such as disodium N-lauryl-β-iminodipropionate or lecithin;

anionic surfactants such as sodium lauryl sulfate, fatty alcohol ether sulfates, mono/dialkyl-polyglycol ether orthophosphoric ester monoethanolamine salt; cationic surfactants such as cetyltrimethylammonium chloride.

Further auxiliaries are agents with which the formulations according to the invention can be sprayed or squirted or rubbed onto the skin. These are the conventional propellent gases required for spray cans, such as propane, butane, dimethyl ether, $CO_2$ or halogenated lower alkanes, or mixtures thereof with one another.

While being of low toxicity to warm-blooded species, the formulations according to the invention are suitable for the control of parasitic insects which are encountered on humans. They are active against all or individual stages of development of the pests and against resistant and normally sensitive species of the pests.

The pests include:

from the order of the Anoplura e.g. Pediculus spp., Pthirus spp.;

From the order of the Siphonaptera e.g. Ctenocephalides spp., Echidnophaga spp., Ceratophyllus spp.

Particular mention may be made of the action against Anoplura and Siphonaptera.

In this connection, the action against Pediculus humanus capitis (head louse), Pediculus humanus corporis (body or clothes louse) and Phthivus pubis (pubic or crab louse) may be mentioned.

The action against mites from the order of the Astigmata, in particular of the families Listrophoridae, Psoroptidae and of the genus Sarcoptes may be mentioned.

The use against Sabgeineus and furthermore the action against ticks such as *Ixodes vicinus* and Rhipicepholus can be both prophylatic and therapeutic.

The formulations according to the invention may additionally comprise juvenile hormones or juvenile hormone-like substances, such as, for example, diaryl ethers, benzoylureas or triazines. These substances include, in particular, compounds of the following formulae:

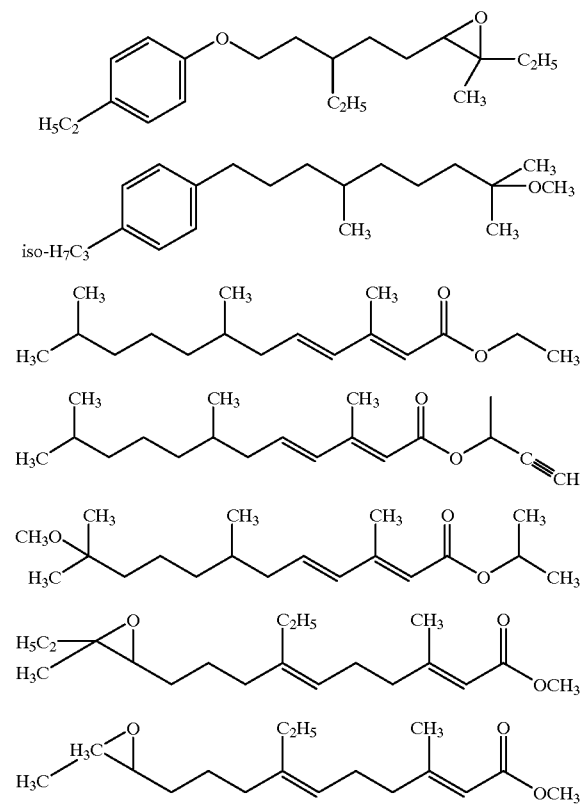

The substituted diaryl ethers include, in particular

| $R^1$ | $R^3$ | $R^5$ | $R^6$ | Z |
|---|---|---|---|---|
| H | H | $CH_3$ | H | O |
| H | H | $CH_3$ | 2-Cl | O |
| 5-F | H | $CH_3$ | H | O |
| H | H | $CF_3$ | H | O |
| H | H | $C_2H_5$ | H | O |
| H | H | H | H | O |
| H | H | $CH_3$ | H | $CH_2$ |
| H | H | $CH_3$ | H | $C(CH_3)_2$ |

The benzoylureas include compounds of the formula

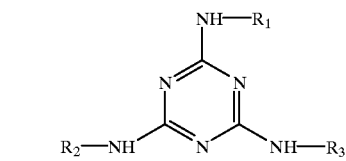

| R¹ | R² | R⁴ |
|---|---|---|
| H | Cl | $CF_3$ |
| Cl | Cl | $CF_3$ |
| F | F | $CF_3$ |
| H | F | $CF_3$ |
| H | Cl | $SCF_3$ |
| F | F | $SCF_3$ |
| H | F | $SCF_3$ |
| H | Cl | $OCF_3$ |
| F | F | $OCF_3$ |
| H | F | $OCF_3$ |
| F | F | —O—C₆H₄—Cl (para) |
| F | F | —O—C₆H₄—CF₃ (para) |
| F | F | —O—C₆H₄—CF₃ (para) |

The triazines include compounds of the formula

| R₁ | R₂ | R₃ |
|---|---|---|
| Cyclopropyl | H | H |
| Cyclopropyl | H | $CH_3$ |
| Cyclopropyl | H | $C_2H_5$ |
| Cyclopropyl | H | $C_3H_7$-n |
| Cyclopropyl | H | $C_4H_9$-n |
| Cyclopropyl | H | $C_5H_{11}$-n |
| Cyclopropyl | H | $C_6H_{13}$-n |
| Cyclopropyl | H | $C_7H_{15}$-n |
| Cyclopropyl | H | $C_8H_{17}$-n |
| Cyclopropyl | H | $C_{12}$—$H_{25}$-n |
| Cyclopropyl | H | $CH_2$—$C_4H_9$-n |
| Cyclopropyl | H | $CH_2CH(CH_3)C_2H_5$ |
| Cyclopropyl | H | $CH_2CH=CH_2$ |
| Cyclopropyl | Cl | $C_2H_5$ |
| Cyclopropyl | Cl | $C_6H_{13}$-n |
| Cyclopropyl | Cl | $C_8H_{17}$-n |
| Cyclopropyl | Cl | $C_{12}H_{25}$-n |
| Cyclopropyl | H | Cyclopropyl |
| Cyclopropyl | H | $COCH_3$ |
| Cyclopropyl | H | $COCH_3$ HCl |
| Cyclopropyl | H | $COC_2H_5$ HCl |
| Cyclopropyl | H | $COC_2H_5$ |
| Cyclopropyl | H | $COC_3H_7$-n |
| Cyclopropyl | H | $COC_3H_7$-i |
| Cyclopropyl | H | $COC_4H_9$-t HCl |
| Cyclopropyl | H | $COC_4H_9$-n |
| Cyclopropyl | H | $COC_6H_{13}$-n |
| Cyclopropyl | H | $COC_{11}$—$H_{23}$-n |
| Cyclopropyl | $COCH_3$ | $COC_2H_5$ |
| Cyclopropyl | $COC_3H_7$-n | $COC_6H_{13}$-n |
| Cyclopropyl | $COCH_3$ | $COC_3H_7$-n |
| Cyclopropyl | $COC_2H_5$ | $COC_3H_7$-n |
| Cyclopropyl | H | COCyclopropyl |
| Cyclopropyl | COCyclopropyl | COCyclopropyl |
| Cyclopropyl | $COCH_3$ | $COCH_3$ |
| Isopropyl | H | H |
| Isopropyl | H | $COCH_3$ |
| Isopropyl | H | $COC_3H_7$-n |
| Cyclopropyl | H | $CONHCH_3$ |
| Cyclopropyl | H | $CONHC_3H_7$-i |
| Cyclopropyl | $CONHCH_3$ | $CONHCH_3$ |
| Cyclopropyl | H | $SCNHCH_3$ |
| Cyclopropyl | H | $CONHCH_2CH=CH_2$ |
| Cyclopropyl | $CONHCH_2CH=CH_2$ | $CONHCH_2CH=CH_2$ |
| Cyclopropyl | $CSNHCH_3$ | $CSNHCH_3$ |

The amount of additional active compounds can be from 0 to 10% by weight based on the total formulation mass, preferably up to 7.5%, particularly preferably up to 5.0%.

Active compounds which can be used for the purposes of the invention include imidacloprid, AKD 1022 and Ti 435.

AKD 1022 is a chloronicotinyl derivative of the formula

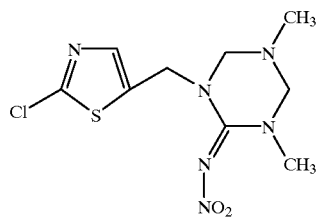

Ti 435 is a chloronicotinyl derivative of the formula

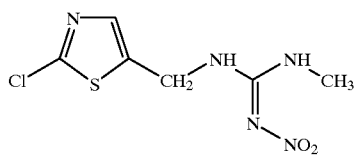

In the examples which follow, the active compound employed is 1-[(6-chloro-3-pyridinyl)methyl]-N-nitro-2-imidazolidinimine (common name imidacloprid).

EXAMPLE 1

| | |
|---|---|
| imidacloprid | 5 g |
| propylene carbonate | 75 g |
| isopropanol | 19 g |
| ®Beisil DMC 6031 | 1 g |

(A polysiloxane copolymer from Wacker GmbH, D-81737 Munich)

EXAMPLE 2

| | |
|---|---|
| imidacloprid | 10 g |
| propylene carbonate | 89 g |
| ®Beisil L 066 | 1 g |

(A polysiloxane copolymer from Wacker GmbH, D-81737 Munich)

EXAMPLE 3

| | |
|---|---|
| imidacloprid | 8.5 g |
| ethanol | 30.0 g |
| ethylene carbonate | 60.5 g |
| ®Beisil L 066 | 1 g |

(Polysiloxane copolymer as spreading agent)

EXAMPLE 4

| | |
|---|---|
| imidacloprid | 10 g |
| tetrahydrofurfuryl alcohol | 30.0 g |
| propylene carbonate | 59.9 g |
| ®Belsil DMC 6031 | 0.1 g |

(Polysiloxane copolymer as spreading agent)

EXAMPLE 5

| | |
|---|---|
| AKD 1022 | 7.5 g |
| isopropanol | 70.0 g |
| propylene carbonate | 22.5 g |

EXAMPLE 6

| | |
|---|---|
| Ti 435 | 10.0 g |
| propylene carbonate | 80.0 g |
| 2-octyl-1-dodecanol | 10.0 g |

EXAMPLE 7

| | |
|---|---|
| imidacloprid | 7.0 g |
| propylene carbonate | 89.0 g |
| isopropyl myristate | 4.0 g |

EXAMPLE 8

| | |
|---|---|
| imidacloprid | 12.5 g |
| benzyl alcohol | 70.0 g |
| propylene carbonate | 17.4 g |
| butylated hydroxytoluene | 0.1 g |

EXAMPLE 9

| | |
|---|---|
| imidacloprid | 5.0 g |
| ethanol | 22.5 g |
| propylene carbonate | 70 g |
| di-2-ethylhexyl adipate | 2.5 g |

EXAMPLE 10

| | |
|---|---|
| imidacloprid | 2.5 g |
| isopropanol | 60.0 g |
| propylene carbonate | 37.5 g |

EXAMPLE 11

| | |
|---|---|
| imidacloprid | 2.5 g |
| pyriproxyfen | 1.0 g |
| isopropanol | 70.0 g |
| propylene carbonate | 26.4 g |
| butylated hydroxytoluene | 0.1 g |

EXAMPLE 12

A spray formulation comprising

| | |
|---|---|
| imidacloprid | 2.5 g |
| isopropanol | 12.5 g |
| propylene carbonate | 60.0 g |
| propane/butane (15:85) | 25.0 g |

EXAMPLE 13

A spray formulation comprising

| | |
|---|---|
| imidacloprid | 2.5 g |
| ethanol | 40.0 g |
| propylene carbonate | 50.0 g |
| $CO_2$ | 7.5 g |

EXAMPLE 14

A spray formulation comprising

| | |
|---|---|
| imidacioprid | 2.5 g |
| ethylene carbonate | 15.0 g |
| propylene carbonate | 15.0 g |
| ethanol | 20.0 g |
| diethyl ether | 47.5 g |

USE EXAMPLE A 2 ml of the formulation described in Examples 1 to 11 were poured onto the backs of dogs weighing about 20 kg which were infested with head lice. The following results were obtained:

The weight of these animals is comparable to the weight of 6- to 8-year-old children.

| Period of time | Number of lice per dog | | |
|---|---|---|---|
| Day | Untreated | Treated | % Action |
| −1 Infestation with 100 lice | | | |
| 0 Treatment and counting | 35 | 0 | 100 |
| 5, 8 Infestation with 100 lice | | | |
| 9 Counting | 53 | 0 | 100 |
| 15 Infestation with 100 lice | | | |
| 16 Counting | 79 | 0 | 100 |
| 19 Infestation with 100 lice (untreated animals) 250 lice (treated animals) | | | |
| 20 Counting | 45 | 0 | 100 |
| 26 Infestation with 100 lice | | | |
| 27 Counting | 42 | 0 | 100 |

Toxicological experiments show that these formulations do not cause any skin irritation in rats and rabbits.

The $LD_{50}$ values of the formulations are >1,800 mg/kg. They have excellent spreading properties on the animal fur. The formulations should therefore also give excellent results in humans.

USE EXAMPLE B 2 ml of the solution according to Examples 12 to 14 were sprayed onto the shoulders of a dog weighing 20 kg. The animal was infested with 200 lice after 2 and after 6 days of treatment. On day 3 and on day 7, respectively, after treatment, the lice remaining on the dog were counted. No living lice were found. Effectiveness was 100%.

Toxicological experiments show that these formulations do not cause any skin irritation in rats and rabbits. They have excellent spreading properties on animal fur and human skin.

What is claimed is:

1. Formulations for the dermal control of parasitic insects and mites on humans, characterized in that they contain agonists or antagonists of the nicotinergic acetylcholine receptors of insects in a concentration of from 0.0001 to 20% by weight based on the overall weight of the formulation;

solvents from the group of the cyclic carbonates in a concentration of from 2.5 to 99.9999% by weight based on the overall weight of the formulation;

optionally solvents from the group of the alcohols in a concentration of from 0 to 95% by weight based on the overall weight of the formulation;

optionally auxiliaries from the group of the thickeners, spreading agents, colorants, antioxidants, propellants, preservatives, adhesives, emulsifiers, in a concentration of from 0 up to 30% by weight based on the overall weight of the formulation.

2. A method of preparing the formulations according to claim 1, characterized in that the agonists or antagonists of the nicotinergic acetylcholine receptors are mixed with the stated solvent(s), and optionally auxiliaries are added.

3. A process for controlling parasitic insects and mites of humans by applying dermally the formulations according to claim 1.

4. A method of preparing the formulations according to claim 1 comprising combining the agonists or antagonists of the nicotinergic acetylcholine receptors of insects with the stated solvent(s).

* * * * *